United States Patent
Guillot

(10) Patent No.: US 9,107,671 B2
(45) Date of Patent: Aug. 18, 2015

(54) COMPRESSIVE HEMOSTATIC DEVICE

(75) Inventor: Romain Christian Guillot, Mionnay (FR)

(73) Assignee: Perouse Medical, Ivry le Temple ( * ) Notice: Subject to any disclaimer, the term of this patent is extended or adjusted under 35 U.S.C. 154(b) by 643 days.

(21) Appl. No.: 13/387,516

(22) PCT Filed: Jul. 26, 2010

(86) PCT No.: PCT/FR2010/051577
§ 371 (c)(1),
(2), (4) Date: Apr. 9, 2012

(87) PCT Pub. No.: WO2011/012805
PCT Pub. Date: Feb. 3, 2011

(65) Prior Publication Data
US 2012/0191127 A1 Jul. 26, 2012

(30) Foreign Application Priority Data

Jul. 31, 2009 (FR) ...................................... 09 55412

(51) Int. Cl.
*A61B 17/00* (2006.01)
*A61B 17/132* (2006.01)

(52) U.S. Cl.
CPC ......... *A61B 17/1325* (2013.01); *A61B 17/1327* (2013.01)

(58) Field of Classification Search
CPC ........... A61B 17/1325; A61B 17/1327; A61B 17/132–17/135; A61B 5/02; A61B 17/12; A61B 17/1322; A61B 17/1355; A61B 5/02233; A61H 9/0078; A61H 2201/5074; A61H 17/1327; A61H 17/1322

USPC .................................................. 606/200–203
See application file for complete search history.

(56) References Cited

U.S. PATENT DOCUMENTS

| 37,156 | A | * | 12/1862 | Dunton | 606/203 |
| 760,846 | A | * | 5/1904 | Border | 246/228 |
| 1,218,313 | A | * | 3/1917 | Plummer | 606/203 |
| 1,281,653 | A | * | 10/1918 | Plummer | 606/203 |

(Continued)

FOREIGN PATENT DOCUMENTS

| DE | 202009005566 U1 | 6/2009 |
| EP | 1 382 306 A2 | 1/2004 |

(Continued)

OTHER PUBLICATIONS

Int'l Search Report & Written Opinion issued in PCT/FR2010/051577 (2010).

*Primary Examiner* — Amy R Weisberg
(74) *Attorney, Agent, or Firm* — Davidson, Davidson & Kappel, LLC

(57) ABSTRACT

The invention relates to a device capable of stopping the bleeding caused by the withdrawal of an introducer stuck into an introduction area of a patient. The device comprises: a base; a supporting means capable of temporarily attaching the base to the patient; an applicator supported by the base and provided with a transparent pad; and a screw-and-nut adjustment means capable of moving the applicator toward the introduction area so that the applicator moves to a position where the pad exerts pressure on the introduction area. The screw-and-nut system is located completely outside the diameter of the transparent pad. The invention can be used for angiography and angioplasty operations.

20 Claims, 12 Drawing Sheets

(56) References Cited

U.S. PATENT DOCUMENTS

| | | | | |
|---|---|---|---|---|
| 1,299,860 | A * | 4/1919 | Plummer | 606/203 |
| 1,322,050 | A * | 11/1919 | Plummber | 24/509 |
| 2,113,534 | A * | 4/1938 | Brown | 606/203 |
| 3,050,064 | A * | 8/1962 | Moore et al. | 606/203 |
| 4,760,846 | A | 8/1988 | Kelly et al. | |
| 5,139,512 | A * | 8/1992 | Dreiling et al. | 606/201 |
| 5,695,520 | A * | 12/1997 | Bruckner et al. | 606/204 |
| 6,833,001 | B1 * | 12/2004 | Chao | 606/203 |
| 7,780,612 | B2 * | 8/2010 | Ross | 602/5 |
| 8,147,417 | B2 * | 4/2012 | Gavriely | 600/499 |
| 8,353,927 | B2 * | 1/2013 | Lampropoulos et al. | 606/204 |
| 2004/0092999 | A1 * | 5/2004 | Lojewski | 606/185 |
| 2004/0122469 | A1 * | 6/2004 | Akerfeldt et al. | 606/201 |
| 2004/0176796 | A1 * | 9/2004 | Akerfeldt et al. | 606/201 |
| 2005/0125025 | A1 * | 6/2005 | Rioux | 606/201 |
| 2008/0177159 | A1 * | 7/2008 | Gavriely | 600/301 |
| 2008/0183207 | A1 * | 7/2008 | Horne | 606/203 |
| 2009/0281565 | A1 * | 11/2009 | McNeese | 606/201 |
| 2010/0010406 | A1 * | 1/2010 | Nardi et al. | 601/152 |
| 2010/0113990 | A1 * | 5/2010 | Chang | 601/41 |
| 2010/0217202 | A1 * | 8/2010 | Clark | 604/180 |
| 2010/0280541 | A1 * | 11/2010 | Lampropoulos et al. | 606/203 |
| 2011/0196417 | A1 * | 8/2011 | Clark | 606/201 |
| 2012/0046582 | A1 * | 2/2012 | Hopman et al. | 602/4 |
| 2012/0089109 | A1 * | 4/2012 | Turner et al. | 604/385.01 |
| 2012/0150215 | A1 * | 6/2012 | Donald | 606/203 |
| 2013/0085524 | A1 * | 4/2013 | Dahlberg et al. | 606/202 |
| 2013/0123836 | A1 * | 5/2013 | Lampropoulos et al. | 606/203 |
| 2013/0310628 | A1 * | 11/2013 | Chisena et al. | 600/15 |
| 2014/0018845 | A1 * | 1/2014 | Lampropoulos et al. | 606/203 |

FOREIGN PATENT DOCUMENTS

| | | |
|---|---|---|
| GB | 08900 | 0/1915 |
| JP | 3087743 | 8/2002 |
| JP | 2004-41599 | 2/2004 |

* cited by examiner

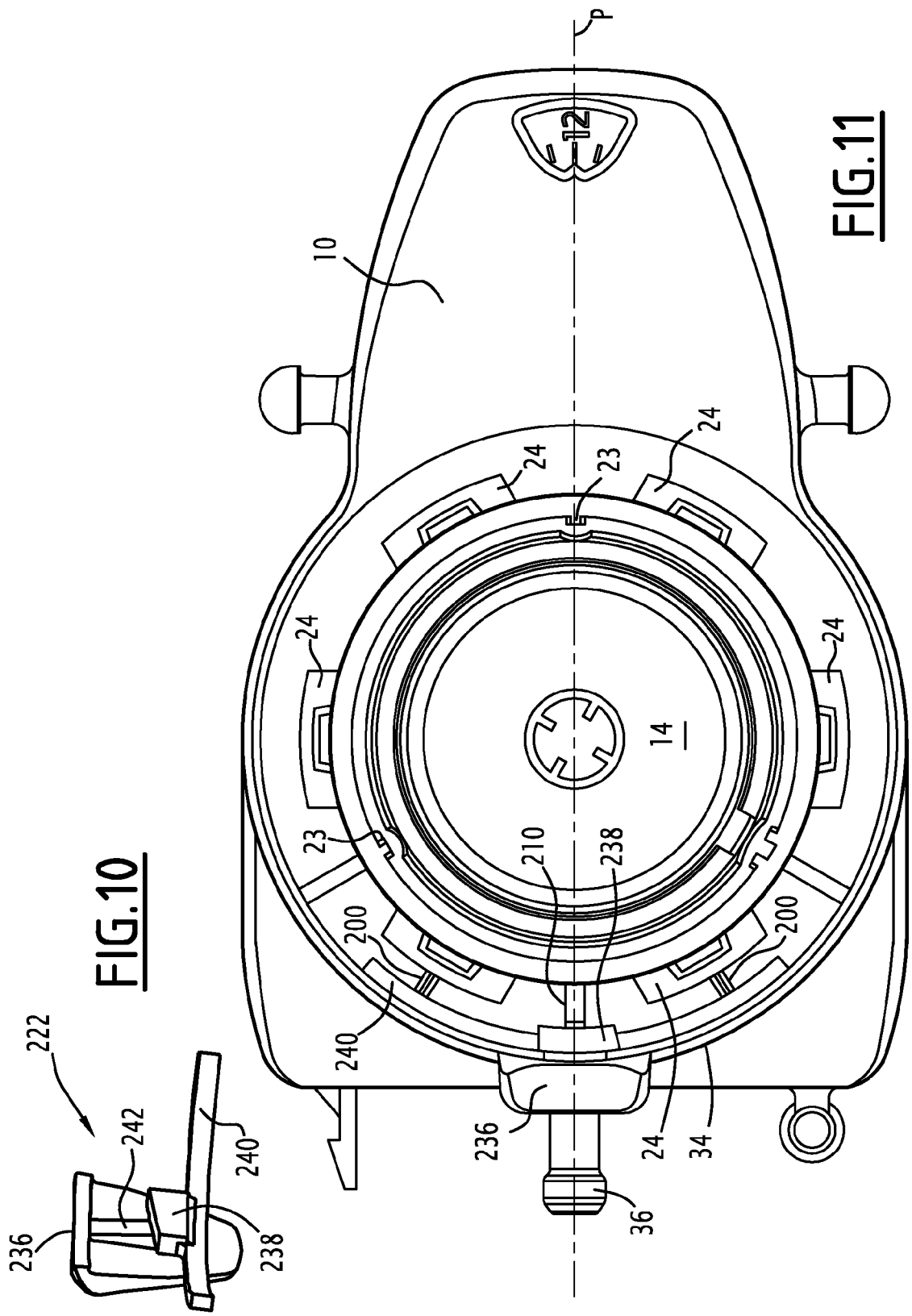

COMPRESSIVE HEMOSTATIC DEVICE

This application is a U.S. nationalization under 35 U.S.C. §371 of International Application No. PCT/FR2010/051577, filed Jul. 26, 2010, which claims priority to French application no. FR0955412, filed Jul. 31, 2009. The disclosures set forth in the referenced applications are incorporated herein by reference in their entireties.

The present invention relates to a compressive hemostatic device of the type described in the preamble of claim 1. This device is in particular adapted to perform the hemostasis of the radial artery for example following an angiography or angioplasty operation without hindering the venous return and without compressing the ulnar artery.

Certain medical imaging methods require a medical operation consisting of injecting a radiological contrast product into the patient's blood system. The contrast is injected through catheters that are passed into an introducer emerging in a blood vessel, the introducer ensuring the sealing of the assembly. For example, the introducer is placed on the inner surface of the patient's wrist so as to allow the introduction of the liquid via the radial artery. Once the operation is completed, removing the introducer while limiting bleeding requires the application of sufficient pressure at the point where the puncture was done, in a zone called introduction or puncture zone. The compression is reduced gradually, until hemostasis of the concerned blood vessel, which can take several hours.

Several devices can be used to obtain such a pressure on the introduction area. For example, document GB 08900 discloses a hemostatic device of the aforementioned type. Practitioners also use devices made up of bandages gripping the introduction area. The device according to GB 08900 and these devices made up of bandages do not allow optimal positioning on the introduction area, due to their opaque nature, or a reliable assessment of the pressure exerted. However, these parameters are fundamentally decisive in the effectiveness of such a device.

Other devices exist, for example of the "TR-BAND®" type by the company TERUMO, assuming the form of a translucent bracelet comprising inflatable pads. The bracelet is positioned around the patient's wrist on the introduction area. A syringe is then used to inflate the pads, which exert pressure on the introduction area. This type of device therefore comprises several elements, which makes caregiver manipulations more complex. Furthermore, these devices also do not allow a reliable and simple assessment of the pressure exerted during placement of the device, or the decompression stop(s).

SUMMARY

The invention aims to propose an autonomous device that can be placed and manipulated by a single operator, at any time, simply and reliably.

Furthermore, in order to best manage the hemostasis, the caregiver must efficiently and reliably monitor the actual decompression time of the patient's introduction area. In fact, not only is it desirable to know the total compression time at all times so that the caregiver can assess the relevance of removing the hemostatic device, but it is also recommended to perform the decompression step in levels.

The devices known to date do not have any particular means making it possible to effectively save the placement time. At the very most, it is possible to write the placement time with a simple pen on the device itself or on the treated area on the patient. The risks of erasure are very real, however, and the caregiver must calculate the removal time unassisted, which can cause harmful calculation errors. Furthermore, monitoring times for several decompression stops can prove particularly difficult, since the aforementioned problems are multiplied by monitoring several patients, and the limited space ends up making the operation too complex.

The invention also aims to propose a time device enabling simple and reliable monitoring of the total placement time of the medical device and/or the length of intermediate steps performed using said medical device, the time device being able in particular to be used on or with a hemostatic device as mentioned above.

To that end, the present invention relates to a compressive hemostatic device of the aforementioned type.

BRIEF DESCRIPTION OF THE DRAWINGS

Other features and advantages of the present invention will better appear upon reading the following description of one embodiment provided as an illustration and non-limitingly in the appended figures, which show:

FIG. 10, a perspective view of an anti-reverse latch of the device of FIG. 9;

FIG. 11, a top view of the device of FIG. 9;

DETAILED DESCRIPTION

Figure 1:
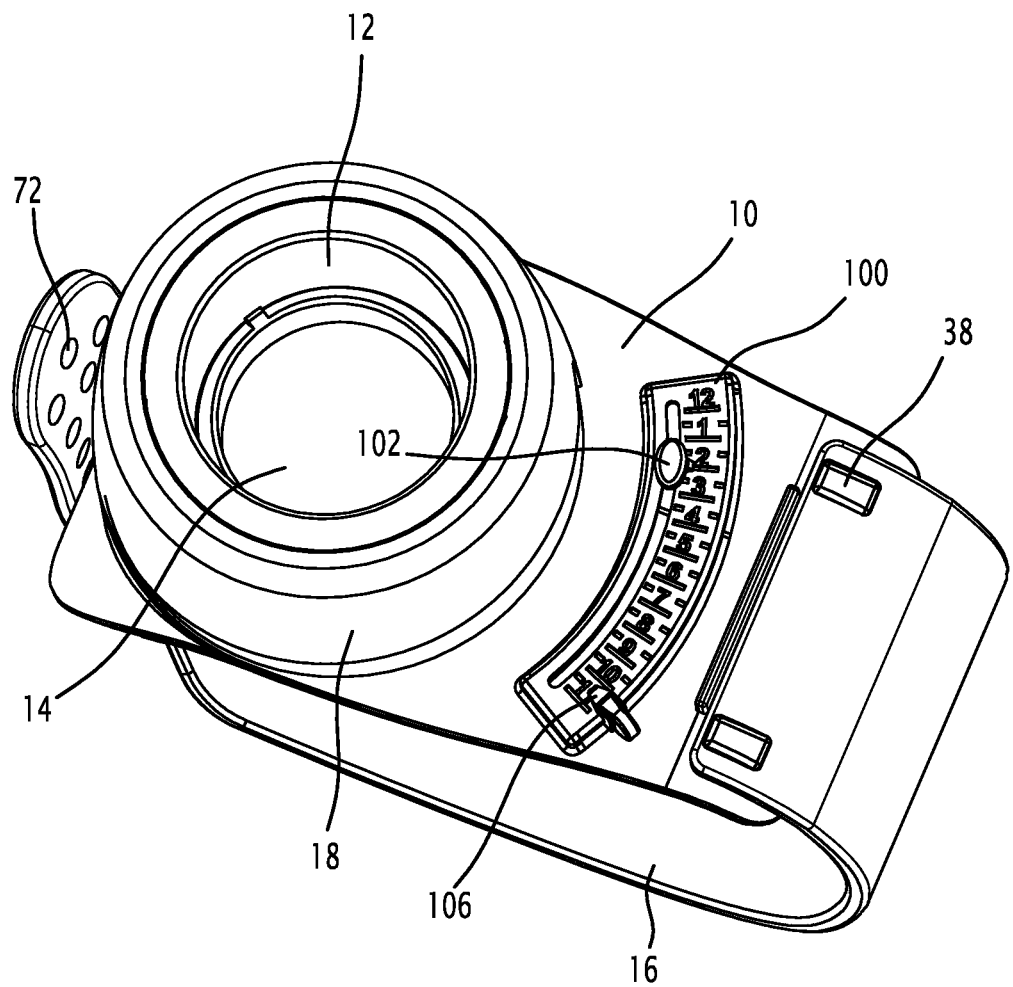
FIG. 1, an overall perspective view of a compressive hemostatic device according to a first embodiment of the invention.

The compressive hemostatic device according to a first embodiment illustrated in FIG. 1 comprises a base 10 on which an applicator 12 is mounted, one of the ends of the latter part comprising a pad 14. A bracelet 16 is fastened on the base 10 making it possible to temporarily secure the base 10 to the patient. The device also comprises a rotary button 18 mounted on the base 10 and cooperating with the applicator 12 so as to translate the latter toward the introduction or puncture zone and vice versa.

Figure 2A:
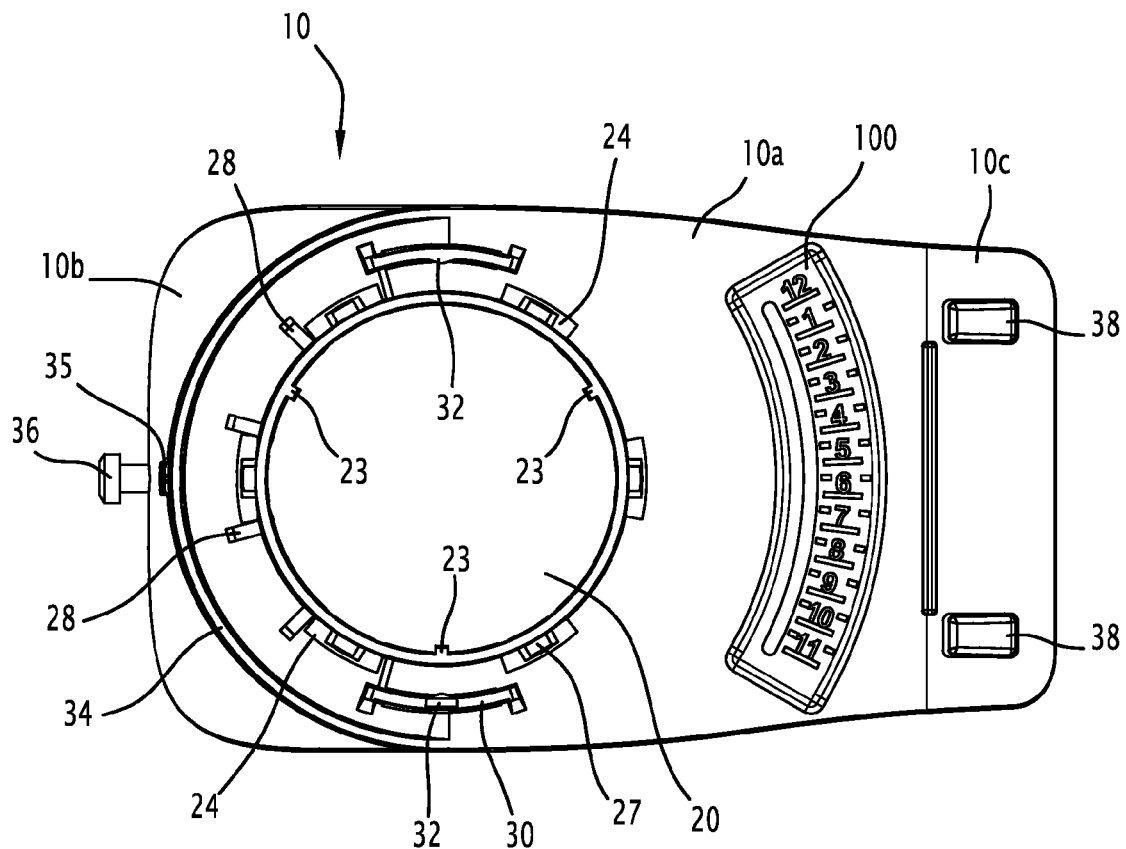
FIGS. 2a and 2b, front and side views of the base of the compressive hemostatic device according to the first embodiment.
Figure 2B:
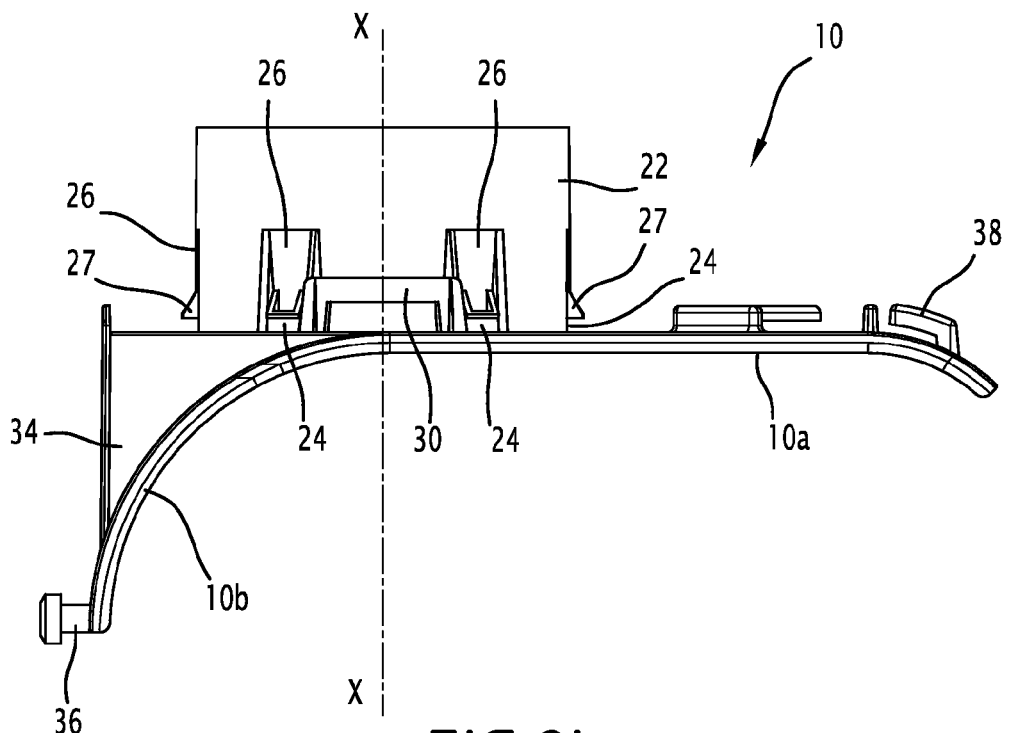

The base 10, as shown in FIGS. 2a and 2b, is formed by a planar part 10a extended by a part 10b curved in an arc of circle. The general shape and the dimensions of the base 10 are chosen so that the base 10 can be positioned ergonomically around the introduction area on the patient's wrist. The base 10 is passed through by a substantially circular recess forming a sighting hole 20, the center of which is situated at the middle of the segment forming the border between the planar part 10a and the curved part 10b.

The sighting hole 20 forms the base of a substantially cylindrical flange 22. The axis X-X of the flange 22, assumed to be vertical for the purposes of this description, is perpendicular to the planar part 10a of the base 10. Three linear guideways 23 extend axially along the entire inner surface of the flange 22. The guideways 23 are equidistant two by two.

Alternatively, one of the guideways can be slightly different or offset so as to index the applicator on the base.

Through holes 24 are formed at the base and around the flange 22 and extend in the adjacent part of the base 10. The through holes 24 are distributed uniformly on the entire periphery of the flange 22. The flange 22 extends in the through holes 24 in assembly clips 26. The assembly clips 26 extend parallel to the axis X-X. Each assembly clip 26 comprises a protrusion 27 at its distal end oriented toward the outside of the flange 22. Each protrusion 27 protrudes relative to the outer surface of the flange 22.

The base 10 comprises, in its curved part 10b and on the periphery of the flange 22, radial stiffening and support ribs 28 for the adjustment button. The ribs 28 rise to the height of the planar part 10a. The planar upper face of the radial ribs 28 is comprised in the same plane as that of the planar part 10a of the base 10.

The base 10 comprises, overlapping the segment forming the border between the planar part 10a and the curved part 10b, two diametrically opposite supports 30 relative to the axis X-X. Each support 30 rises vertically. The side faces of each support 30 form an arc of circle centered on the axis X-X. Each support 30 is elastically deformable and comprises, on its inner side face, a gadroon or pawl protrusion 32.

The curved part 10b of the base 10 comprises a hollow semi-cylindrical extension 34 with longitudinal axis X-X. The extension 34 rises to the height of the plane of the planar part 10a. The extension 34 has a diameter substantially equal to the length of the segment forming the border between the planar part 10a and the curved part 10b.

The base 10 comprises, at the end of its curved portion 10b, a fastening lug 36. The base 10 comprises, at the end of its planar portion 10a, an extension 10c supporting two hooks 38.

Figure 3A:
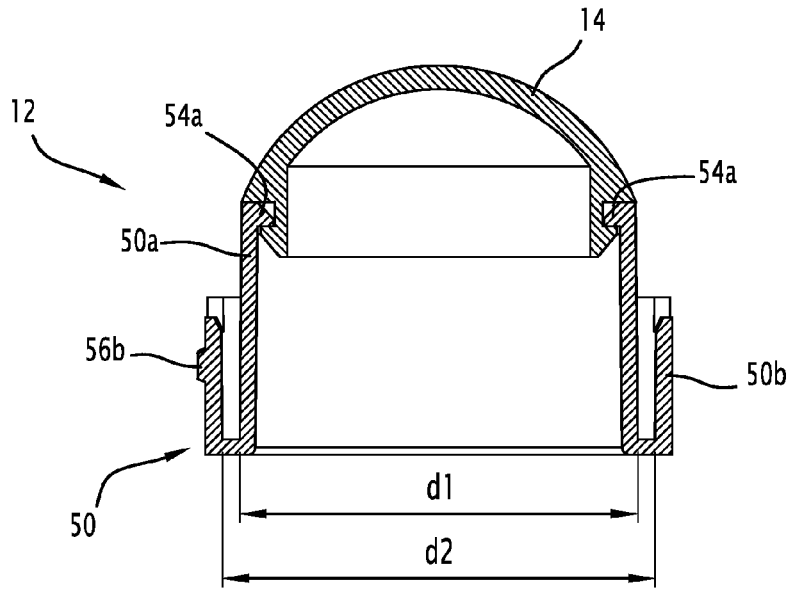
FIGS. 3a and 3b, side and axial cross-sectional views of the applicator of the compressive hemostatic device according to the first embodiment.
Figure 3D:
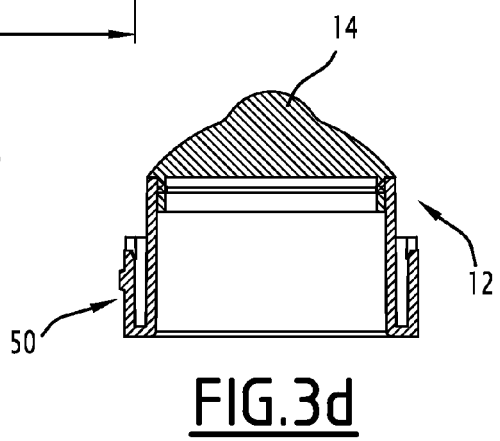
FIGS. 3c and 3d, a planar view and an axial cross-sectional view along line IIId-IIId of FIG. 3c, respectively, of one applicator alternative.
Figure 3B:
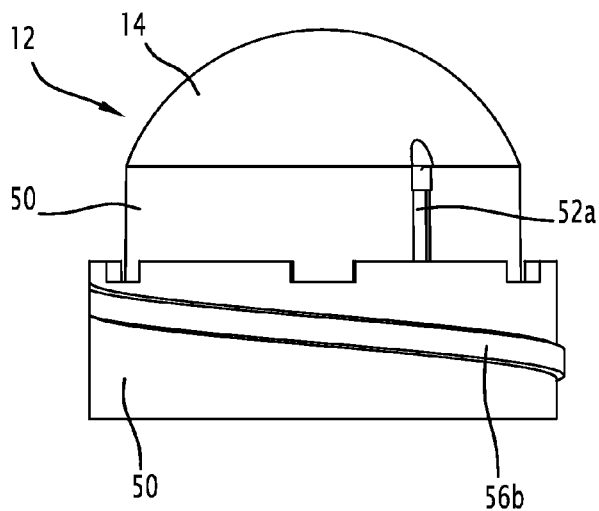

As illustrated in FIGS. 3a and 3b, the applicator 12 comprises a support 50. The support 50 is formed by a cylindrical inner tube 50a with an outer diameter $d_1$ and a cylindrical outer tube 50b with an inner diameter $d_2$. The two tubes 50a and 50b are coaxial and connected by their bases. The outer diameter $d_1$ is chosen so as to be substantially equal to the inner diameter of the flange 22 of the base 10. The inner diameter $d_2$ is chosen so as to be substantially equal to the outer diameter of the flange 22. The lengths of the tube 50a and the tube 50b are chosen as a function of the desired movement amplitude for the applicator 12 when the button 18 is actuated.

The tube 50a comprises three recesses 52a extending longitudinally in the outer face of the first tube 50a. The recesses 52a are sized and positioned so as to cooperate with the guideways 23 of the flange 22 of the base 10 when the support 50 is mounted in the flange 22. The tube 50a comprises an inner flange 54a at its free end cooperating with a circular recess formed in the pad 14 so as to secure the latter part to the support 50. The outer face of the tube 50b comprises a protruding screw thread 56b.

Alternatively, the tube 50b can have two threads "fitted" one into the other to reliabilize the screwing and distribute the tightening forces.

The pad 14 is made from a transparent material. The spherical dome bearing shape of the pad 14 is chosen so as to maximize the patient's comfort while reducing the risk of blocking the venous return on the other veins located nearby.

Figure 3C:
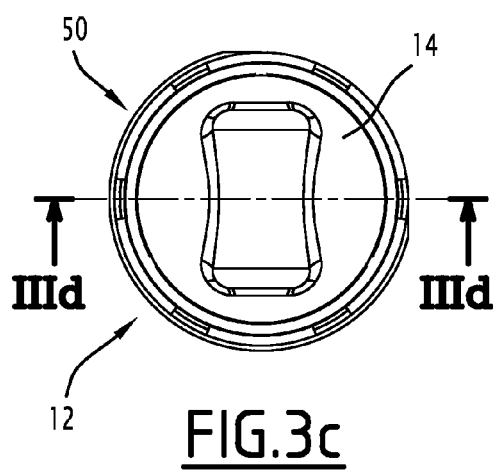

Alternatively, the bearing shape of the pad can be different from a spherical dome, in particular oblong and particularly semi-cylindrical, as shown in FIGS. 3c and 3d, so as to follow the groove of the wrist where the radial artery is located.

Figure 4A:
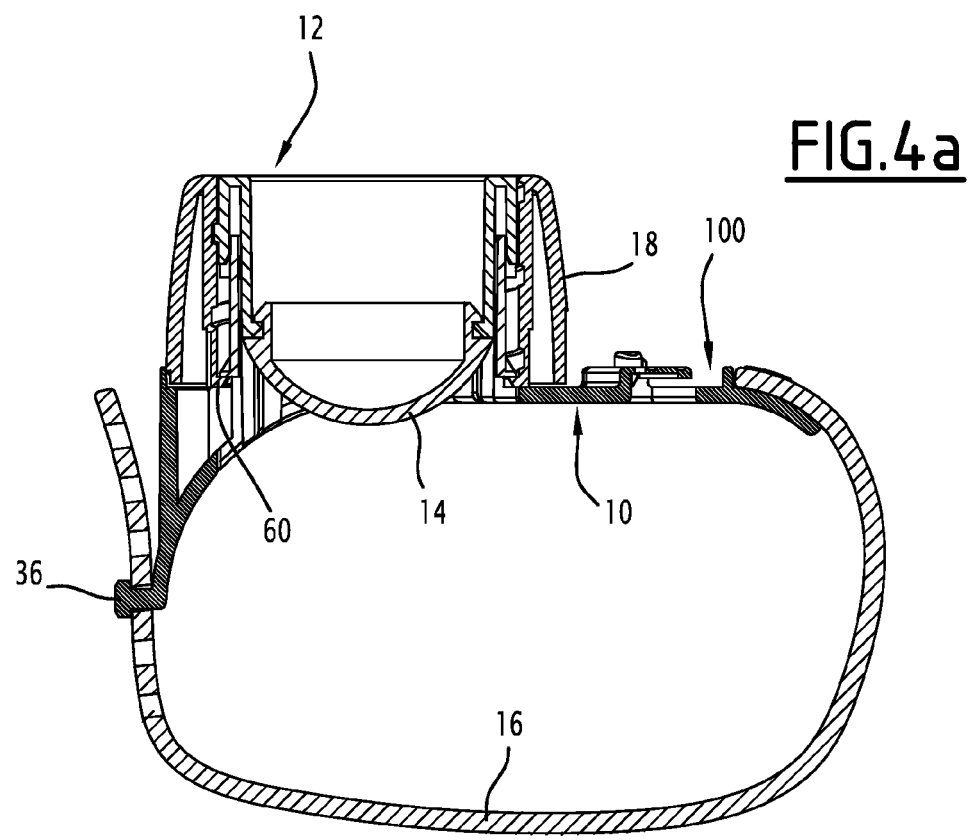
FIG. 4a, a lateral cross-section of the compressive hemostatic device according to the first embodiment.
Figure 4B:
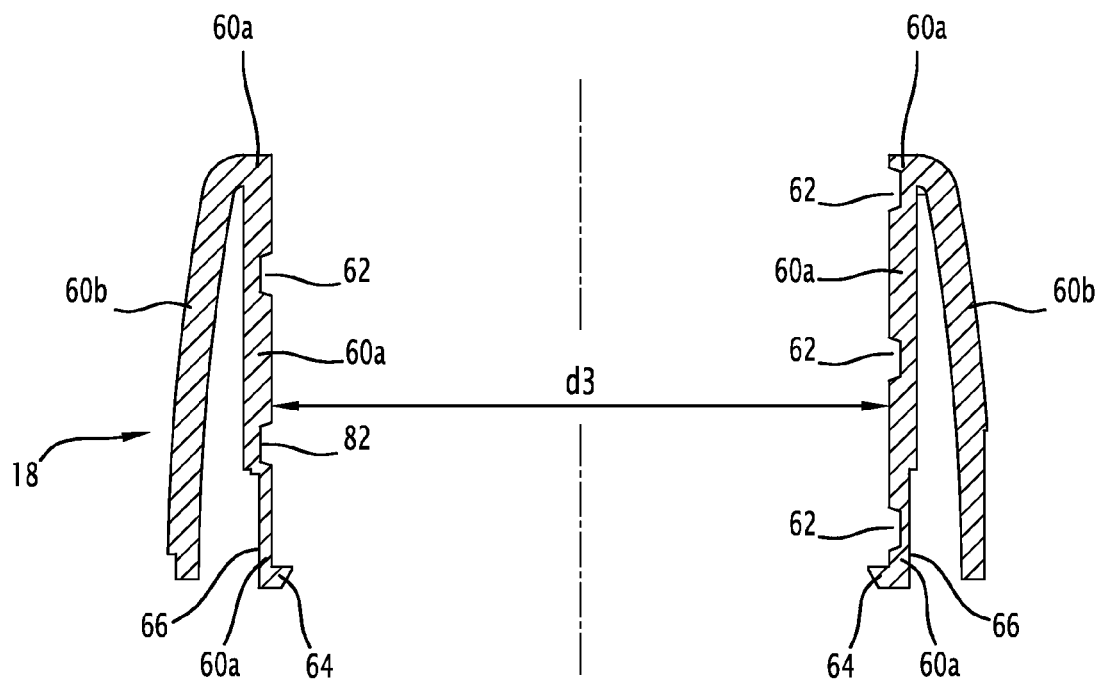
FIG. 4b, an axial cross-sectional view of the button of the compressive hemostatic device according to the first embodiment.

As illustrated in FIGS. 4a and 4b, the button 18 is formed by a cylindrical inner tube 60a outwardly provided with a substantially conical gripping member 60b making it possible to facilitate handling of the button 14 by an operator. The cylindrical tube 60a has an inner diameter $d_3$ substantially equal to the outer diameter of the outer tube 50b of the support 50 of the applicator 12. The inner face of the cylindrical tube 60a comprises a hollow screw pitch 62 capable of cooperating with the or each screw thread 56b of the applicator 12. The cylindrical inner wall of the button 18 also comprises, at its base, a protruding inner skirt 65, the dimensions and arrangement of which are chosen so as to cooperate, once the button 18 is mounted on the base 10, with the assembly clips 26 thereof so as to block the translation of the button 18 along its longitudinal axis, but to leave the button 18 freely rotating around that same axis. Notches 66 are regularly arranged on the entire outer surface of the cylindrical tube 60a so that they are capable of cooperating with the pawl gadroon 32 of the two ribs 30 when the button 18 is mounted on the base 10, to form stop means making it possible to maintain the button in a plurality of predetermined stable angular positions. If desired, to differentiate the force to be exerted on the button in the two directions, the notches can be asymmetrical.

To facilitate the production of the button, the lower part of the button, comprising the skirt 64 and the notches 66, could be another piece assembled (adhered or welded, for example) on the rest of the button.

Once assembled, the applicator 12, the button 18 and the base 10 are thus connected by a screw-and-nut system so that the rotation of the button translates the transparent pad. The screw threads 56b, 62 of the screw-and-nut system are situated completely outside the diameter of the transparent pad 14. As a result, the view through the transparent pad 14 on the introduction area is not hidden.

Figure 5:
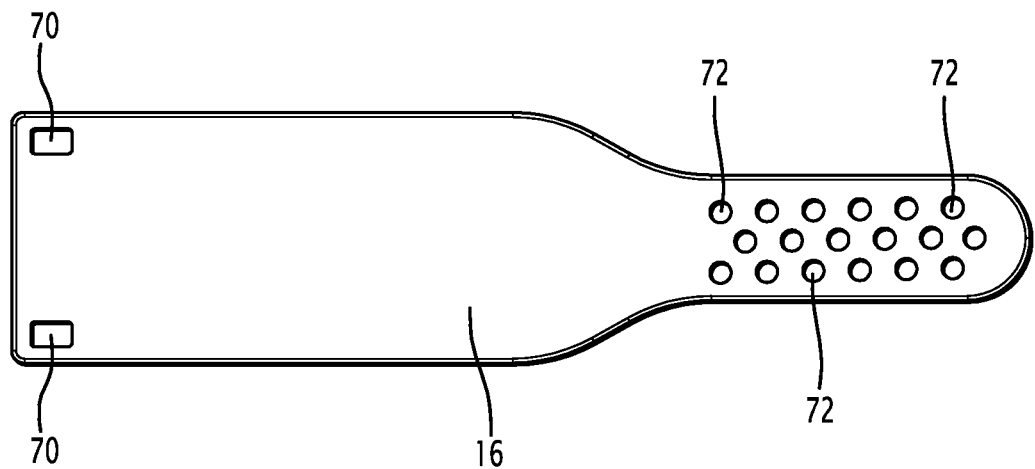
FIG. 5, a frontal view of a bracelet according to the first embodiment.

As shown in FIG. 5, the bracelet 16 comprises, at one of its ends, two perforations 70, the shape and arrangement of which make it possible, in cooperation with the hooks 38 of the base 10, to secure said end to the base. The other end of the bracelet 16 comprises a plurality of through holes 72, each able to cooperate with the fastening lug 36 to secure said end to the base 10, the choice of the through hole making it possible to adjust the tightening of the bracelet 16 around the patient's wrist.

Alternatively, the button 18 could be directly screwed into a hole of the base 10, with the proximal end of the applicator 12 secured at least in translation to the button.

Figure 6A:
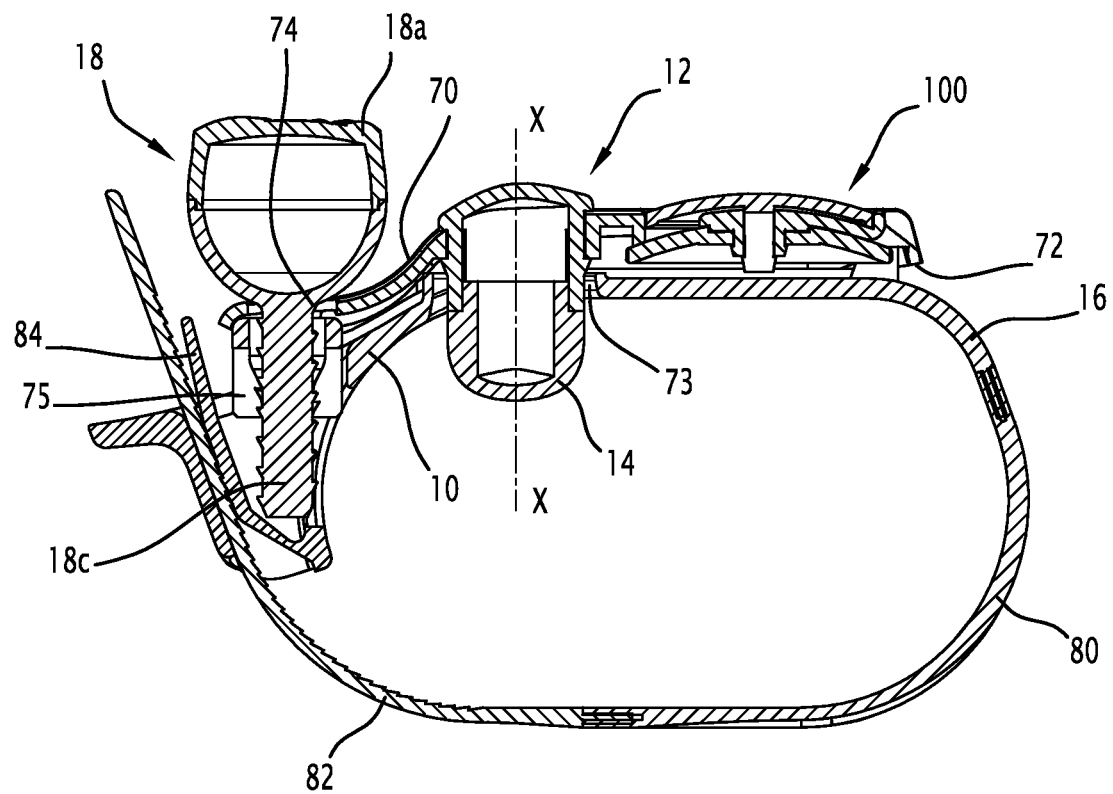
FIGS. 6a, 6b, 6c, a lateral cross-section, a side view and a front view of the compressive hemostatic device according to a second embodiment of the invention.
Figure 6B:
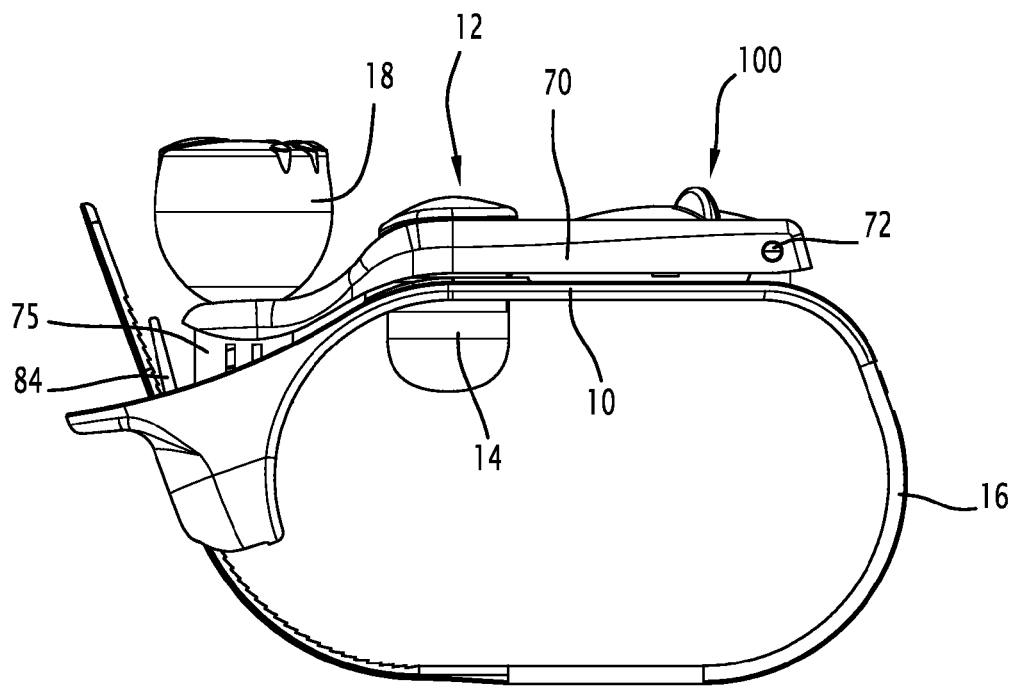
Figure 6C:
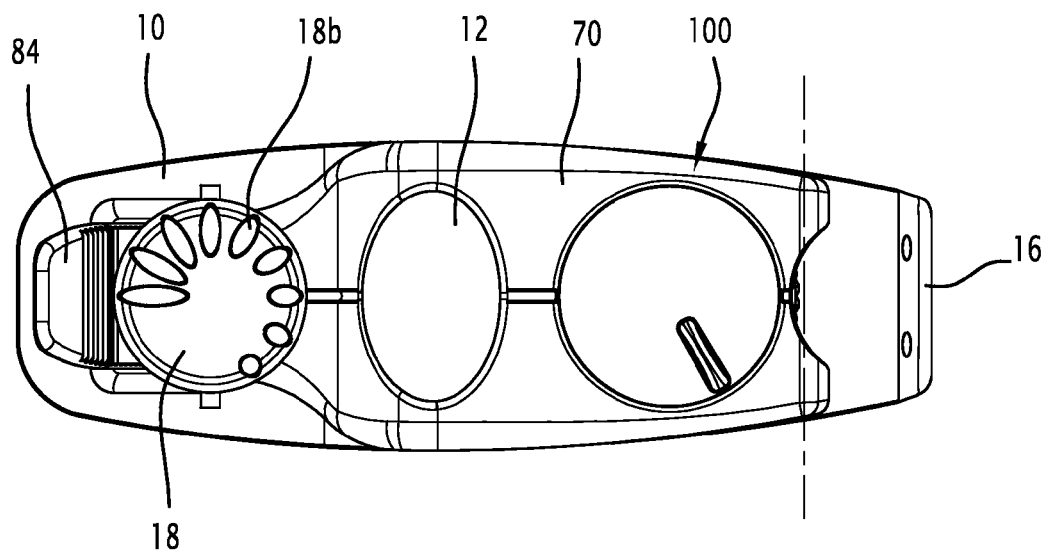

In a second embodiment of the compressive hemostatic device according to the invention, shown in FIGS. 6a, 6b and 6c, the proximal end of the applicator 12, which is completely transparent, is secured to a platen 70 whereof one end is connected to the base 10 by a hinge 72. The applicator, with axis X-X, passes freely through an orifice 73 of the base. The other end of the platen 70 has a hole 74 parallel to the axis X-X.

The button 18 comprises an upper portion 18a forming the head of the button 18, on which angular references 18b are positioned. The button 18 comprises a lower portion 18c forming a threaded rod passing through the hole 74 and screwed into a nut 75 secured to the portion 10b of the base 10.

Advantageously, the nut 75 is designed so as to be able to deform enough to allow the translation of the button along its longitudinal axis when pressure is exerted along that axis on the head 18a by a user, thereby making it possible to move the button 18 more quickly than by screwing. To that end, the thread of the nut 75 can comprise flexible strips and be made from a material offering sufficient elasticity.

The bracelet 16 comprises a flexible bracelet 80 whereof one end is secured to an end of the base 10 and extends the latter, the other end comprising a notched zone 82. The notched zone is capable of cooperating with a locking/unlocking lever 84 provided at the proximal end of the base provided with the nut 75. The lever 84 tends to assume its locking position elastically.

Advantageously, the pad 14 protrudes relative to the base 10 toward the introduction area irrespective of the position defined by the adjustment button. This guarantees that pressure is obtained on the introduction area in all cases during placement of the device.

Advantageously, the device according to the invention can comprise means for saving placement and removal times, allowing the person handling the device to save the time at which the device was placed on the patient, as well as the time at which the device must be removed or was actually removed. The means for saving placement and removal times can advantageously be positioned on the base 10.

Figure 7A:
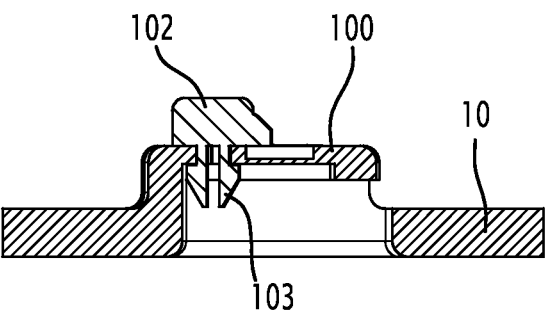
FIGS. 7a, 7b, 7c, two lateral cross-sectional views and a front view of the means for saving the placement and removal times according to a first embodiment.
Figure 7B:
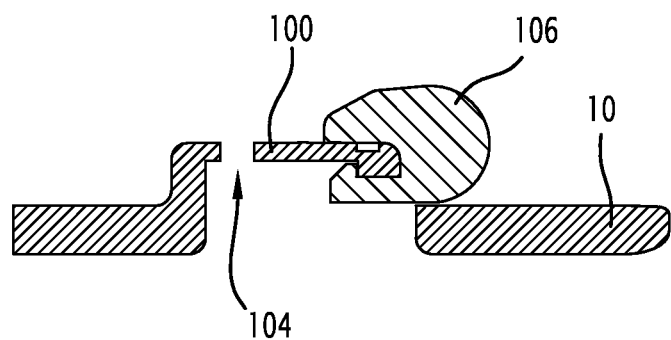
Figure 7C:
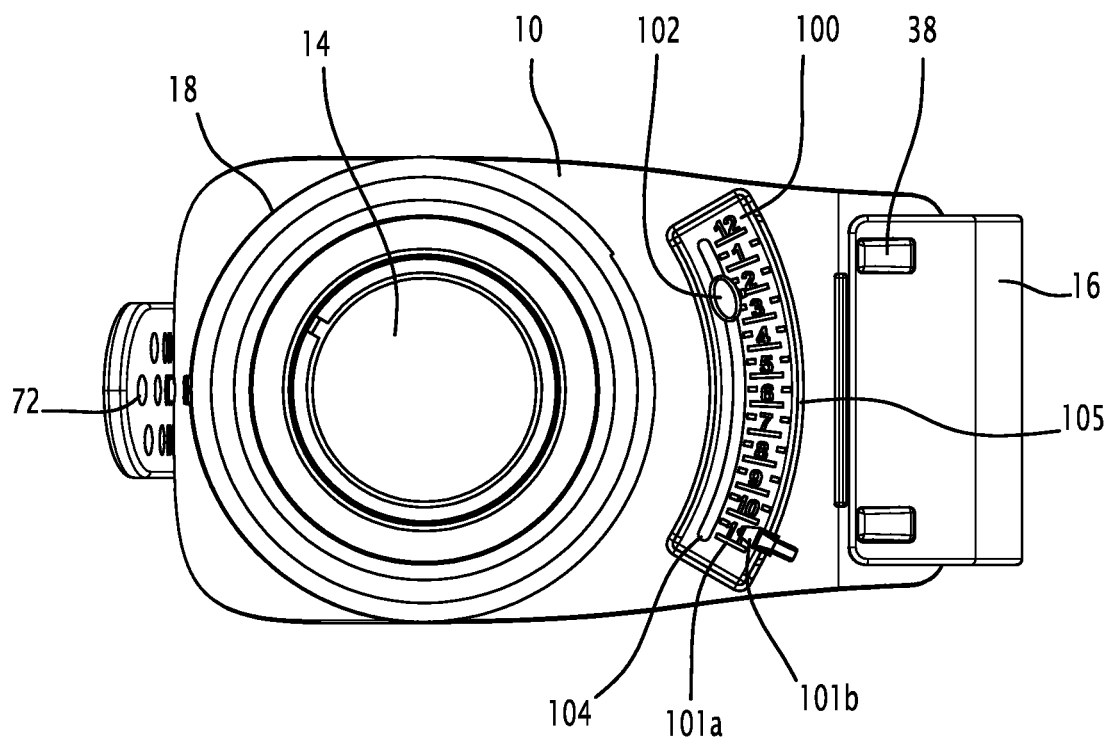

In a first embodiment illustrated in FIGS. 7a, 7b and 7c, the means for saving the placement and removal times comprise a bowed ruler 100, centered on the axis X-X, on which graduations 101a, 101b appear. Each graduation corresponds to a mark for the corresponding time. Typically, the marks go from 12 to 11, representing a time scale going from 12 hours to 11 hours, as shown in FIG. 7c. The ruler 100 comprises a first inner notched guideway 104. A pin 102 provided with assembly clips 103 is mounted in the guideway 104. The pin 102 can move frictionally in the guideway 104 and be maintained in a plurality of fixed positions each corresponding to one of the marks of the inner graduation 101a. The ruler 100 comprises a second notched outer guideway 105 on which a pointer 106 slides. The pointer 106 can move frictionally in the second notched guideway and be positioned in a plurality of fixed positions each corresponding to one of the marks of the outer graduation 101b. Notches provided in the two guideways can alternatively define predetermined stable positions of the pin 102 and the pointer 106.

Figure 8A:
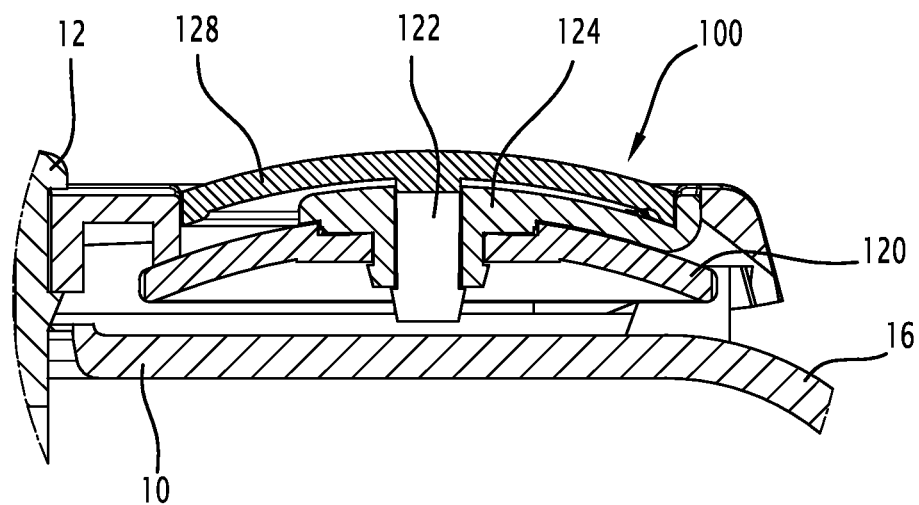
FIGS. 8a, 8b, a lateral cross-sectional view and a front view of the means for storing placement and removal times according to a second embodiment.
Figure 8B:
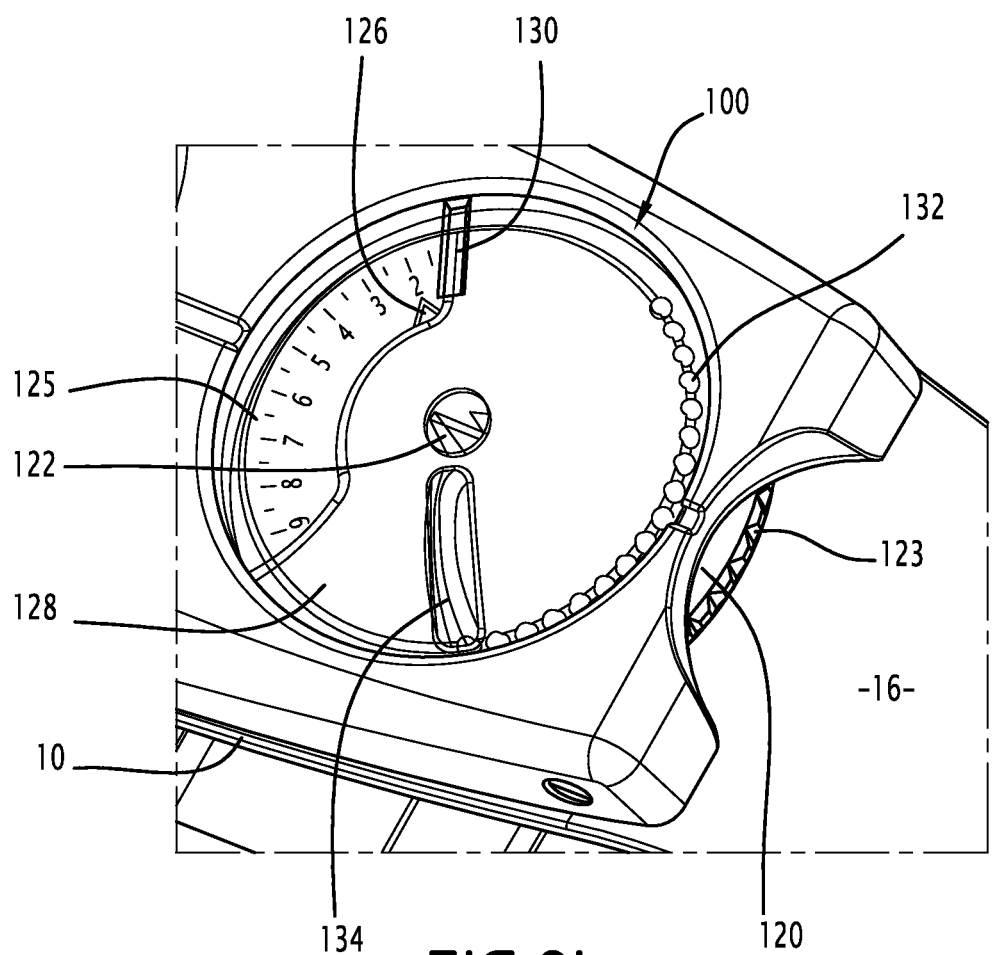

In a second embodiment illustrated in FIGS. 8a and 8b, the means 100 for saving the placement and removal times comprise a dial 120 rotatably mounted around an axis 122. Hour references are marked on the dial 120, for example from 1 hour to 24 hours. A knurled peripheral part 123 of the dial is accessible to the user so that the latter can rotate the dial 120. The dial 120 is partially concealed by a fixed opaque disk 124 covering the dial 120. The opaque disk 124 also comprises a fixed index 126 positioned so as to allow pointing to a time reference of the dial 120 not covered by the opaque disk 124. The part of the dial 120 left visible by the opaque disk 124 corresponds to a circular sector zone 125 whereof the dimensions make it possible to view a set of time references of the dial 120 corresponding to an hour range of 8 hours from the hour pointed to by the fixed index 126. Also rotatably mounted around the axis 122 is a transparent disk 128 covering the opaque disk 124. The transparent disk 128 is provided with a pointer 130 arranged so that a user can identify an hour mark of the dial 120 not covered by the opaque disk 124. Indexing notches 132 are positioned on the opaque disk 124 and the transparent disk 128 so as to index the rotation of the transparent disk 128 over a plurality of predetermined angular positions. To facilitate the rotation of the transparent disk 128 by a user, a bulge 134 is positioned on the surface of the transparent disk 128.

The user can thus store the placement and implementation time of the device on the patient by rotating the dial 120 until the mark of the dial 120 corresponding to said placement time is designated by the fixed index 126. The user can indicate the removal time of the device by rotating the transparent disk 128 until the pointer 130 designates the mark of the dial 120 corresponding to said removal time.

Alternatively, in each embodiment, one and/or the other of the hour indicators can reference a change time, done or to be done, of the pressure exerted by the device.

A combination of the two embodiments of the saving means illustrated in FIGS. 7a to 7c and 8a-8b can be considered.

It is also alternatively possible to produce a device comprising only one hour graduation.

Figure 9:
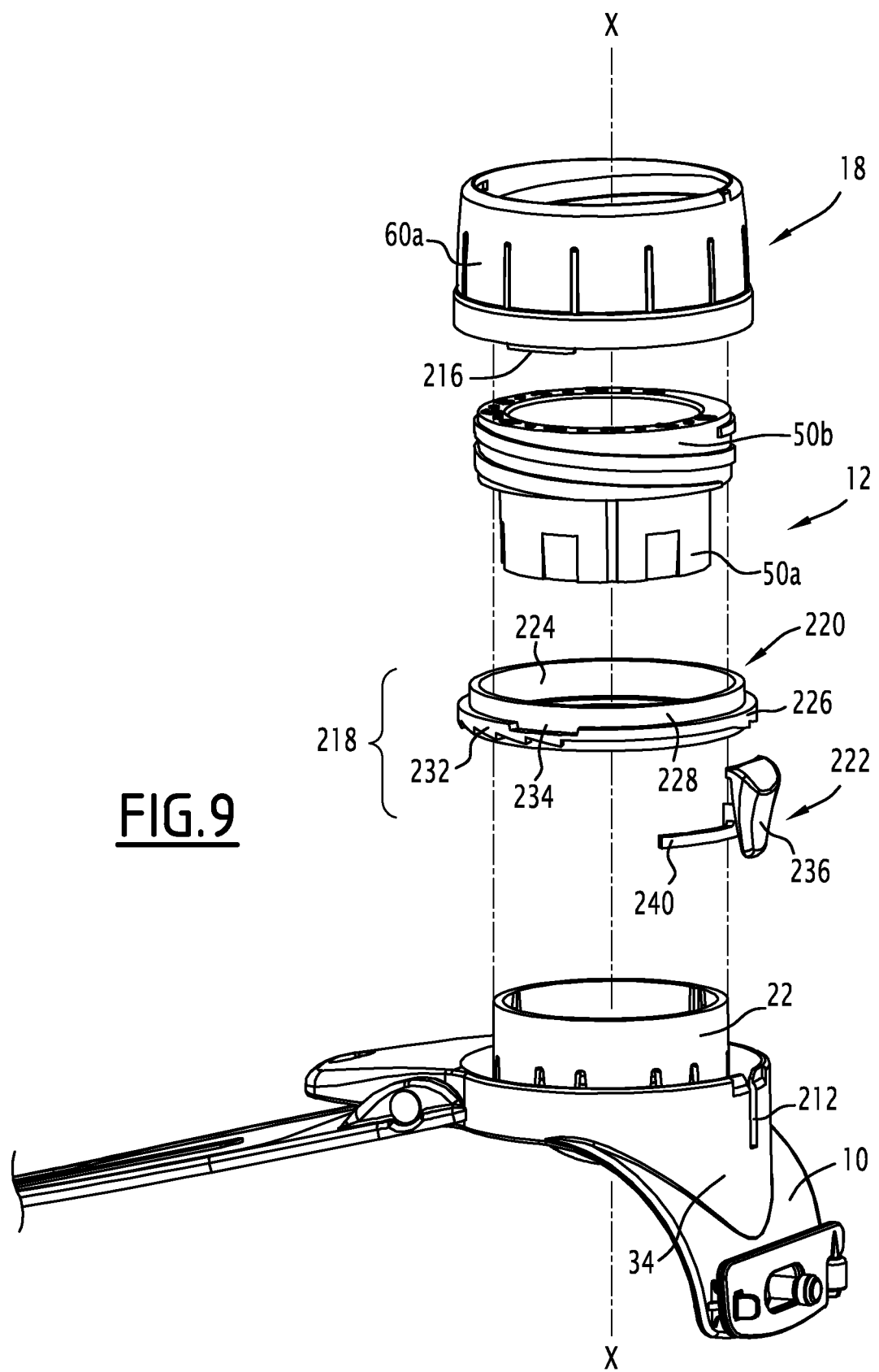
FIG. 9, an exploded view of the compressive hemostatic device according to a third embodiment of the invention, the transparent pad not being shown.

A third embodiment of the hemostatic device is shown in FIGS. 9 to 14. This device differs from the first embodiment only as follows:

the base 10 does not comprise the supports 30 with the pawl protrusions 32, but two outer vertical supports 200 and an intermediate vertical support 210, protruding from the base 10 toward the button 18. The support 210 is located in the vertical plane of symmetry P of the device, and the supports 200 at about 30° on either side of that plane.

the extension 34 rises above the plane of the planar portion 10a of the base 10, is circular, and has a vertical slot 212 in plane P;

the button 18 does not comprise a gripping member 60b, but only the inner cylindrical tube 60a, said tube 60a also being a gripping member; and the cylindrical tube 60a does not have the notches 66, or the protruding inner skirt 64, but comprises, in its portion oriented toward the base 10 (FIGS. 13 and 14), an inner recess 214 and at least one tab 216 that protrudes vertically from the button 18 toward the base 10 (FIG. 9).

Relative to the first embodiment, the third embodiment of the hemostatic device also comprises a locking system 218.

The locking system 218 comprises a ring 220 and an anti-reverse latch 222. The ring 220 is placed in the annular space situated between the flange 22 and the extension 34.

The ring 220 comprises an inner cylindrical ring 224 and an outer toothed crown 226. The ring 220 is a single piece. The ring 220 is made from a copolymer, for example ABS. The ring 224 and the toothed crown 226 extend concentrically around the longitudinal axis X-X. The toothed crown 226 surrounds the ring 224. The latter protrudes vertically from the toothed crown 226 toward the button 18 while forming a flange 228. The ring 224 has, in its portion oriented toward the base 10, a protruding inner skirt 230, the function of which is similar to that of the corresponding skirt 64 of the button 18 of the first embodiment: by cooperating with the clips 26 of the base, the skirt 230 blocks the translation of the ring 220 along the longitudinal axis X-X, but leaves the ring 220 freely rotating around the same axis.

The crown 226 has, on its end section oriented toward the base 10, saw-teeth 232 oriented vertically. The teeth 232 are regularly distributed over the entire periphery of the toothed crown 226. Alternatively, the teeth 232 are regularly distributed over a part corresponding to 180° or 270° of the periphery of the crown 226. In its portion oriented opposite the base, the crown 226 has at least one notch 234 (FIG. 9).

Figure 13:
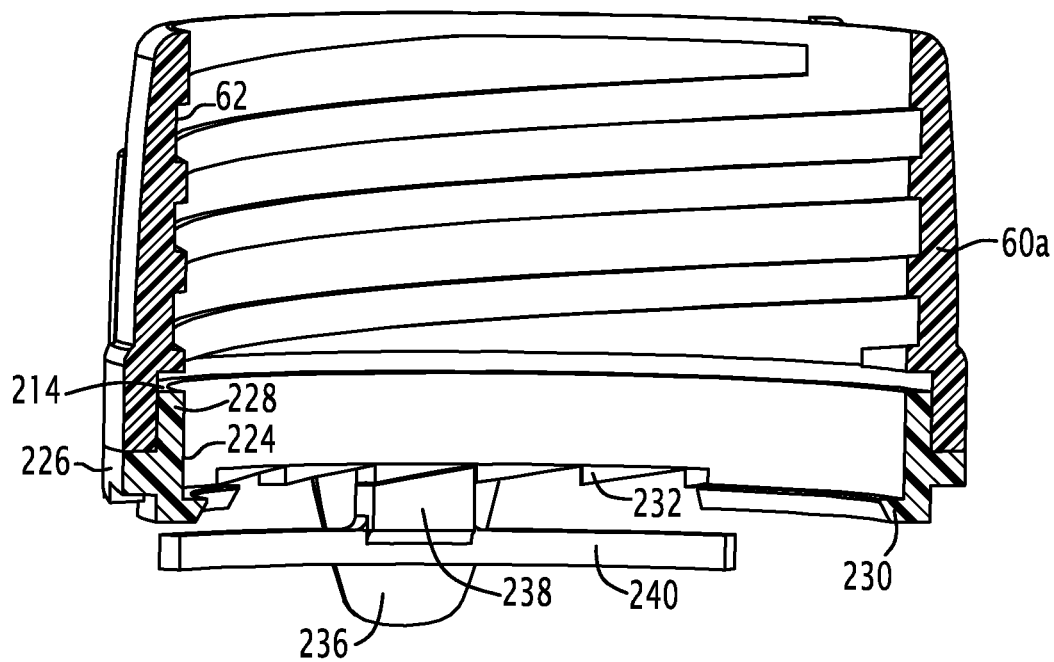
FIG. 13, an axial cross-section of the button of the device of FIG. 9 with the anti-reverse latch of FIG. 10 in the locking position.
Figure 14:
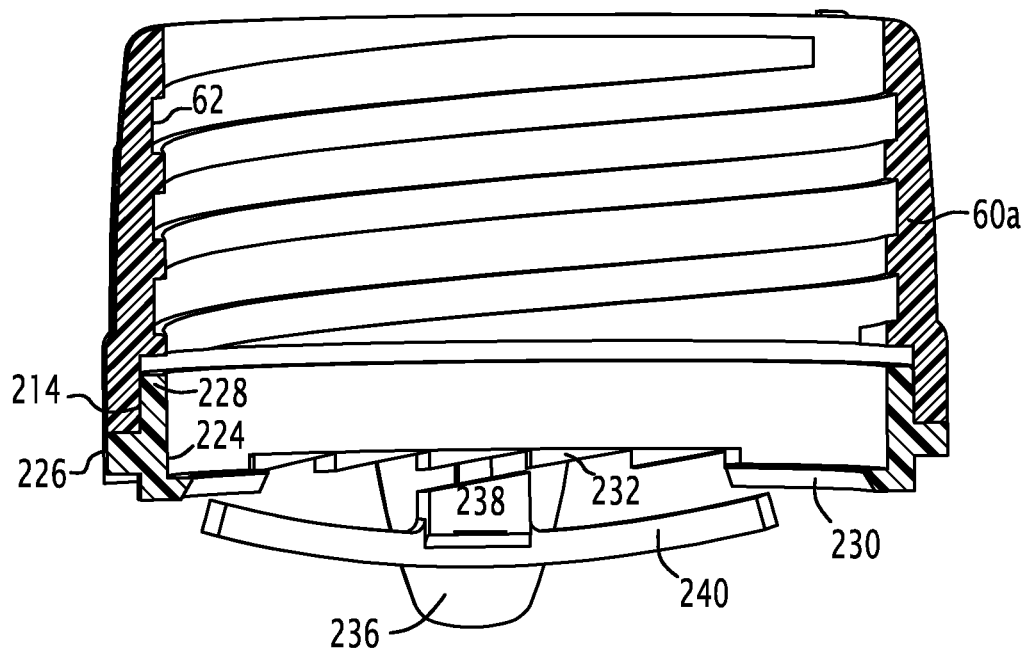
FIG. 14, an axial cross-section similar to that of FIG. 13, but with the anti-reverse latch in the unlocking position.

The flange 228 of the ring 220 has an outer diameter adapted for frictional tightening in the recess 214 of the cylindrical tube 60a of the button 18 (FIGS. 13 and 14). The or each notch 234 of the ring 220 is adapted to cooperate with the or each tab 216 of the button 18. In this way, the ring 220 is secured in rotation to the button 18 around the axis X-X.

The applicator 12 and its transparent pad 14 are substantially identical to those of the first embodiment.

Alternatively, the ring 220 and the button 18 are connected to one another by adhesion or ultrasound welding.

The anti-reverse latch 222 comprises a push button 236, a locking pawl 238, a bowed arm 240, and a vertical rib 242 (FIG. 10). The latch 222 is a single piece and is made from a polymer, such as POM.

The push button 236 is connected to the pawl 238 via the vertical rib 242. It is adapted to move the pawl 238 parallel to the axis X-X between a blocking position and an unblocking position. The pawl 238 has, in its portion oriented opposite the base, a shape complementary to that of one of the teeth 232 of the toothed crown 226, so as to be able to cooperate with each of the teeth 232. The portion oriented toward the base 10 of the pawl 238 is substantially connected to the central portion of the bowed arm 240.

Figure 12:
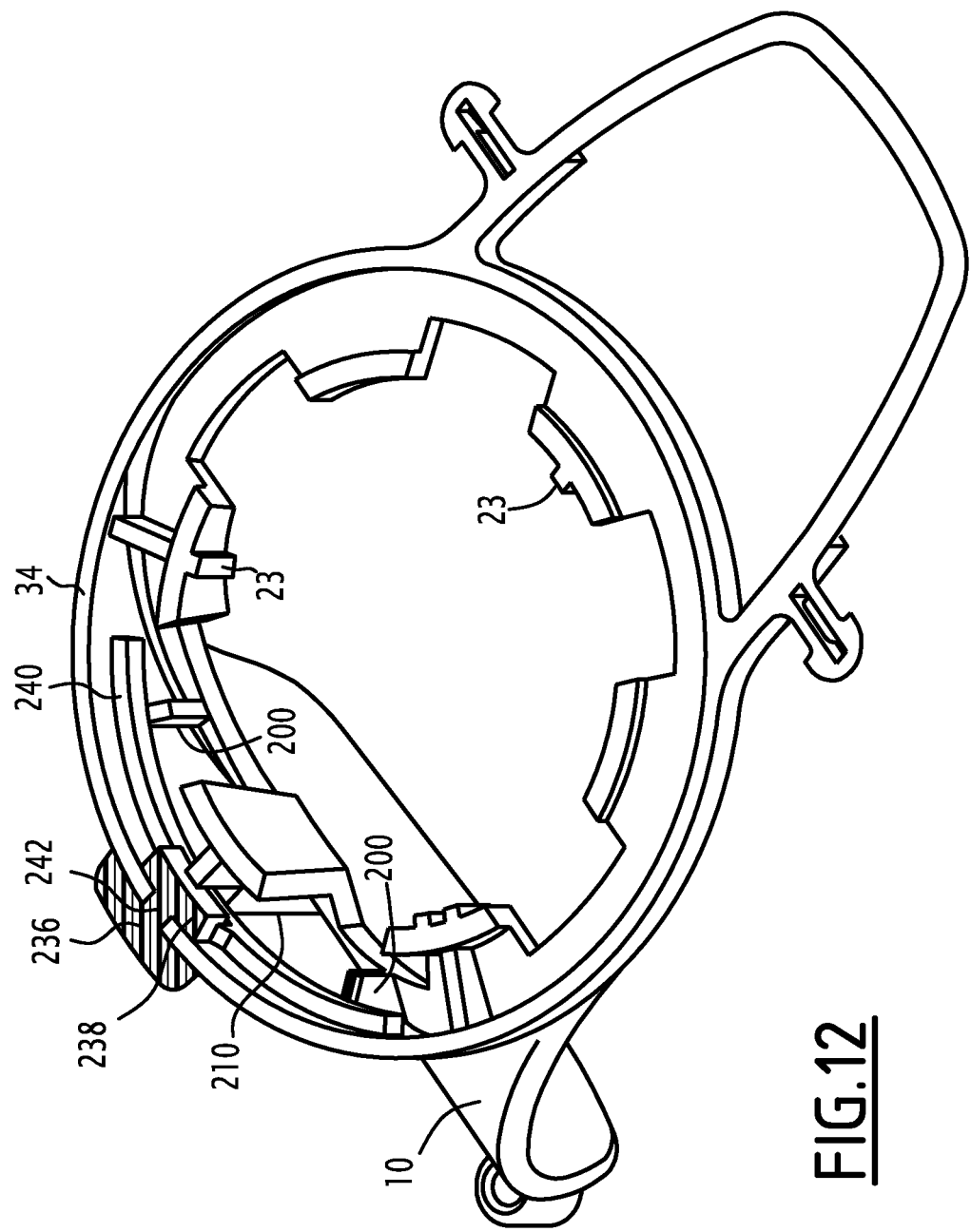
FIG. 12, a perspective view of the anti-reverse latch of FIG. 10 positioned on the base of the device of FIG. 9.

In the blocking position, the bowed arm 240 extends substantially in a plane perpendicular to the axis X-X on either side of the pawl 238 (FIG. 12). The bowed arm 240 describes an arc of circle having a diameter equal to or larger than the outer diameter $d_1$ of the inner tube 50a of the applicator 12.

The vertical slot 212 present in the extension 34 of the base 10 rises above the plane of the planar portion 10a of the base and is open opposite the base (FIG. 9). The slot 212 has a width and length adapted to receive the vertical rib 242 of the latch 222 so that the push button 236 slidingly bears against the outer face of the extension 34 and the pawl 238 and the bowed arm 240 slidingly bears against the inner face of the extension 34 (FIG. 11). Consequently, the push button 236 is accessible by a user, while the pawl 238 and the bowed arm 240 are not.

Furthermore (FIG. 11), the end portions of the arm 240 overhang the supports 200 of the base.

As shown in FIG. 11, the anti-reverse latch 222 is located completely outside the diameter of the transparent pad 14.

FIG. 12 shows the two outer vertical supports 200 and the intermediate vertical support 210, protruding from the base toward the button 18. The support 210 protrudes from the base 10 to a lower height than the supports 200. The height of the supports 200, 210 is such that the bowed arm 240 bears only against the outer supports 200 when the pawl 238 is in the blocking position, and the arm 240 is continuously bent, i.e. when the pawl 238 is in the blocking position or the unblocking position.

When the pawl 238 is in the blocking position (FIG. 12), the part of the pawl oriented opposite the base 10 is bearing against one of the teeth 232 of the toothed crown 226. The incline of the teeth 232 enables the unidirectional rotation around the axis X-X of the ring 220 and therefore the button 18 when the pawl 238 is in this blocking position. In this example, the rotation of the button 18 is blocked in the direction of rotation driving the applicator 12 and the pad 14 opposite the introduction area, while the rotation in the opposite direction, driving the applicator 12 and the pad 14 toward the introduction area, is not blocked. The bowed arm 240 only bears on the supports 200.

To allow the rotation of the button 18 in the first aforementioned direction, i.e. to reduce the pressure exerted by the pad 14, the user presses the push button 236, against the elastic force exerted by the bowed arm 240. This brings the pawl 238 into the unblocking position (FIG. 14), in which it is not in contact with the teeth 232 of the toothed crown 226. The bowed arm 240 is then vertically curved and bears against the intermediate support 210. When the pawl 238 is in the unblocking position, the ring 220 and therefore the button 18 are free to rotate in both directions around the axis X-X. In that position, it is therefore possible to drive the applicator 12 and the pad 14 opposite the introduction area so as to reduce the pressure exerted on that zone.

In order to reduce the pressure of the pad 14 exerted on the introduction area, it is crucial to bring the anti-reverse latch 222 into the unblocking position and rotate the button 18 in the corresponding direction. These two maneuvers are difficult or impossible to do with one hand, for example by a patient wearing the hemostatic device around a wrist.

The locking system 218 is positioned completely outside the diameter of the pad 14 so as not to conceal the view through the transparent pad 14 on the introduction area. This allows a user to position the hemostatic device according to the invention optimally on the introduction area of a patient.

The invention claimed is:

1. A compressive hemostatic device capable of stopping bleeding caused by withdrawal of an introducer stuck into an introduction area of a patient, in particular to perform hemostasis of a radial artery, the device comprising:
    a base;
    a support capable of temporarily attaching the base to the patient;
    an applicator supported by the base and provided with a pad; and
    an adjuster capable of moving the applicator toward the introduction so that the applicator moves relative to the base to a position where the pad exerts pressure on the introduction area, the base comprises a through sighting hole supported by the support opposite the introduction area, the pad being transparent and movable in the sighting hole, and in that the adjuster is situated completely outside a diameter of the transparent pad such that the introduction area is viewable through the transparent pad.

2. The device according to claim 1, wherein the adjuster comprises a button rotatably mounted on the base around a longitudinal axis (X-X) of the sighting hole, the applicator, the button and the base being connected by a screw-and-nut system so that rotation of the button causes the translation of the applicator along the longitudinal axis (X-X);
    and wherein the screw-and-nut system comprises screw threads of the applicator and the button cooperating together, the screw threads being situated completely outside the diameter of the transparent pad.

3. The device according to claim 2, wherein the screw threads are provided on an outer face of the applicator and on an inner face of the button.

4. The device according to claim 1, wherein the pad protrudes relative to the base toward the introduction area irrespective of its position defined by the adjuster.

5. The device according to claim 1, wherein the base and the button comprise a cooperating stop making it possible to maintain the button in a plurality of predetermined stable angular positions.

6. The device according to claim 1, comprising a locking system adapted to block rotation of the button in one of the two directions of rotation of said button.

7. The device according to claim 6, wherein the locking system is a unidirectional locking system adapted to block rotation of the button in a direction of rotation driving translation of the applicator opposite the introduction area.

8. The device according to claim 6, wherein the locking system comprises a locking member able to move between a blocking position and an unblocking position.

9. The device according to claim 8, wherein the locking member is movable parallel to said longitudinal axis (X-X).

10. The device according to claim 9, wherein the locking member is secured to a bowed arm that bears on the base to ensure an elastic return of the locking member toward its blocking position.

11. The device according to claim 6, wherein the locking system is situated completely outside the diameter of the transparent pad.

12. The hemostatic device according to claim 1, whereof the support comprises a bracelet secured to the base.

13. The device according to claim 1, comprising a time reference configured for saving the time at which said compressive hemostatic device was placed on the patient or the time elapsed since that moment.

14. The device according to claim 13, also comprising a time reference configured for saving the time at which the pressure exerted by the compressive hemostatic device has been or must be modified or the time elapsed since that moment.

15. The device according to claim 1, comprising a time reference configured for saving the time at which said compressive hemostatic device must be withdrawn from the patient or the duration remaining until that moment.

16. A compressive hemostatic device capable of stopping bleeding caused by withdrawal of an introducer stuck into an introduction area of a patient, in particular to perform hemostasis of a radial artery, the device being of the type comprising:
   a base;
   a support capable of temporarily attaching the base to the patient;
   an applicator supported by the base and provided with a pad, the applicator further comprising a cylindrical inner tube having a first end and a second end, the pad being secured to the second end of the cylindrical inner tube; and
   an adjustor capable of moving the applicator toward the introduction so that the applicator moves relative to the base to a position where the pad exerts pressure on the introduction area,
   the base further comprising a through sighting hole, supported by the support opposite the introduction area, the pad being transparent and movable in the sighting hole, the cylindrical inner tube delimiting an inner space from the first end to the second end, the inner space being empty from the first end of the tube to the transparent pad, the adjuster being situated completely outside a diameter of the transparent pad such that the introduction area is viewable through the transparent pad.

17. A compressive hemostatic device capable of stopping the bleeding: caused by the withdrawal of an introducer stuck into an introduction area of a patient, in particular to perform the hemostasis of the radial artery, the device being of the type comprising:
   a base;
   a support capable of temporarily attaching the base to the patient;
   an applicator supported by the base and provided with a pad; and
   an adjuster capable of moving the applicator toward the introduction area so that the applicator moves relative to the base to a position where the pad exerts pressure on the introduction area, the base comprises a through sighting hole supported by the support opposite the introduction area, the pad being transparent and movable in the sighting hole, the adjuster being situated completely radially outside the diameter of the transparent pad such that the introduction area is viewable through the transparent pad.

18. The device according to claim 17, wherein the adjuster comprises a button rotatably mounted on the base around a longitudinal axis (X-X) of the sighting hole, the applicator, the button and the base being connected by a screw-and-nut system so that rotation of the button causes translation of the applicator along the longitudinal axis (X-X);
   and wherein the screw-and-nut system comprises screw threads of the applicator and the button cooperating together, the screw threads being situated completely outside the diameter of the transparent pad.

19. The device according to claim 18, wherein the screw threads are provided on an outer face of the applicator and on an inner face of the button.

20. The device according to claim 17, wherein the pad protrudes relative to the base toward the introduction area irrespective of its position defined by the adjuster.

* * * * *